US009302086B2

(12) United States Patent
Won

(10) Patent No.: US 9,302,086 B2
(45) Date of Patent: Apr. 5, 2016

(54) DERMATOLOGICAL DRUG INJECTING DEVICE

(76) Inventor: Yong-Ki Won, Icheon (KR)

( * ) Notice: Subject to any disclaimer, the term of this patent is extended or adjusted under 35 U.S.C. 154(b) by 150 days.

(21) Appl. No.: 14/115,885

(22) PCT Filed: Nov. 21, 2011

(86) PCT No.: PCT/KR2011/008864
§ 371 (c)(1),
(2), (4) Date: Nov. 6, 2013

(87) PCT Pub. No.: WO2013/047949
PCT Pub. Date: Apr. 4, 2013

(65) Prior Publication Data
US 2014/0094742 A1 Apr. 3, 2014

(30) Foreign Application Priority Data
Sep. 26, 2011 (KR) .................. 10-2011-0097153

(51) Int. Cl.
A61M 37/00 (2006.01)
A61M 5/32 (2006.01)

(52) U.S. Cl.
CPC ........... A61M 37/00 (2013.01); A61M 37/0076 (2013.01); A61M 5/3287 (2013.01); A61M 5/3298 (2013.01)

(58) Field of Classification Search
CPC .................. A61M 37/0076; A61M 5/3298
See application file for complete search history.

(56) References Cited

U.S. PATENT DOCUMENTS

2010/0030152 A1  2/2010  Lee et al.
2012/0041374 A1  2/2012  Lee

FOREIGN PATENT DOCUMENTS

| KR | 10-2003-0017533 A | 3/2003 |
| KR | 10-0819468 B1 | 4/2008 |
| KR | 10-0922138 | * 10/2009 |
| KR | 10-0922138 B1 | 10/2009 |
| KR | 10-0972800 B1 | 7/2010 |
| KR | 10-0973628 B1 | 8/2010 |

* cited by examiner

Primary Examiner — Kevin C Sirmons
Assistant Examiner — Deanna K Hall
(74) Attorney, Agent, or Firm — Rabin & Berdo, P.C.

(57) ABSTRACT

The present invention relates to a dermatological drug injecting device, and more particularly, to a dermatological drug injecting device that can use a needle to treat wrinkles, dry skin, scars, freckles, hair loss, etc. on human skin, or to use ink to inscribe images or characters. To achieve said technical aims, a dermatological drug injecting device of the present invention installed on a skin maintenance apparatus comprises: a body portion installed on a fixing portion of a drug injecting device of the skin maintaining apparatus; a connecting driveshaft portion installed on the body portion and moved linearly; an actuating portion installed on the body portion and moved linearly by means of the connecting driveshaft portion; and a needle fixing portion installed on the actuating portion.

12 Claims, 8 Drawing Sheets

DERMATOLOGICAL DRUG INJECTING DEVICE

CROSS-REFERENCE TO RELATED APPLICATION

This application claims priority from Korean Patent Application No. 10-2011-0097153 filed on Sep. 26, 2011 in the Korean Intellectual Property Office, the disclosure of which is incorporated herein by reference in its entirety.

TECHNICAL FIELD

The present invention relates to a dermatological drug injecting device, and in particular to a dermatological drug injecting device which makes it possible to treat wrinkles, keratin, scar, melasma, dried and split skins, hair loss, etc. in a human body and makes it possible to inscribe images or characters using pigments.

BACKGROUND ART

A drug injecting device for human skin has been generally used as a means for a skin and health care, an obesity care, etc., in details, for the sake of wrinkle and acne removal, keratin removal, alopecia treatment, etc. The above mentioned treatment consists of a method in which a hole is formed at a skin, and a drug or cosmetic is applied to over the hole so as to help the applied drug penetrate fast and enough to have a great effect on medication, and a method in which a needle is forced to stimulate skins so that collagen can be produced with the aid of a reaction operation of a human body.

Numerous holes may be formed on a human skin using a needle in a shape of a certain pattern or an image such as a symbol, letter and graphic, and then various colorful pigments are applied to over the holes to help the pigments effectively penetrate for thereby finishing a tattoo.

For example, a new skin grows in the middle of a recovery of a skin tissue damaged during the formations of the numerous holes at a human body, and a treatment drug is applied to over the numerous holes, so that the drug can penetrate fast into the skin through the numerous holes.

The above mentioned dermatological drug injecting device helps grow and rearrange a new corium tissue with the aid of a natural scar treatment operation which naturally happens while a plurality of needles are penetrating into the skin, for which a scan grows shallow, and a treated skin keeps tensioned for thereby removing small wrinkles and a pigment deposition is improved, and a treated person can have a clean and healthy skin.

There are many kinds of devices which are capable of forming small holes at a skin when injecting a certain drug into a skin.

A Korean patent registration number 10-0973628 discloses "a combined device for skin."

The above mentioned Korean patent registration number 10-0973628 has features in that a slope guide surface is formed on an inner surface of a cylindrical cam rotating by means of a driving motor, and a cam block at one side of which a roller disposed at an inner side of a cylindrical cam and rolling along a slope guide surface is engaged actuates up and down a needle with the aid of a connection lever, so the needle can move forth and back forming holes at a skin.

However, the above described conventional system is configured in such a way that as an engaging method of a needle engaging part which forms holes at a skin, the needle engaging part and a slider keep being engaged by means of a flat spring.

In the above configuration, it is impossible to quickly disengage the needle engaging part from the slider when it needs to exchange the damaged needle engaging part.

When vibrations occurs through the operations of the driving motor, the needle engaging part may disengage from a needle depth adjusting part in the middle of work, which may cause an accident.

The connection lever connected to the driving motor and the holder activating the needle are connected through a connection part, so the operations of the driving motor are transferred to the connection lever, and the operations transferred to the connection lever is transferred to the holder. In this case, it is hard to assemble and disassemble the needle engaging part. Since the operations of the driving motor is directly transferred to the needle, the impacts are directly transferred to the skin for thereby causing pains.

DISCLOSURE OF INVENTION

Accordingly, the present invention is made to improve the problems encountered in the conventional art. It is an object of the present invention to provide a dermatological drug injecting device which makes it possible to easily install and disengage a drug injecting device at/from a combined device for skin in such a way the drug injecting device is engaged or disengaged now what an engaging protrusion is formed at a slider of a combined device for skin and an engaging hole to/from which the engaging protrusion formed at the slider is engaged or disengaged in the dermatological drug injecting device.

It is another object of the present invention to provide a dermatological drug injecting device which makes it possible to quickly exchange a drug injecting device when it is damaged, in such a way that a drug injecting device can be engaged to or disengaged from a combined device for skin with the aid of a protrusion and a groove.

It is further another object of the present invention to provide a dermatological drug injecting device which has features in that a connection shaft advances when a connection lever advances in a state that it is contacting with a connection lever which is configured to transfer the operations of the driving motor of the combined device for skin, and when the connection lever moves backward, the connection shaft elastically recovers by means of an elastic force of an elastic member, with the aid of which construction the connection lever and the connection shaft can be easily disassembled or assembled, and the connection shaft can return back by means of the elastic member, so the connection shaft can work reliably.

It is still further another object of the present invention to provide a dermatological drug injecting device which has features in that a plurality of needles are equipped, which help form at a time multiple holes at a skin, so it is possible to inject drug into many portions for short time.

It is still further another object of the present invention to provide a dermatological drug injecting device which has features in that a curved groove is formed at one side of a body of a body part, so the body of the body part can come closer to a skin in an easier way, and it can move along the skin without leaving any scar at the skin.

To achieve the above objects, there is provided a dermatological drug injection device which is engaged to a combined device for skin, comprising a body part which is engaged to a dermatological drug injecting device fixing part of the combined device for skin; a connection driving shaft part which is installed at the body part and linearly moves; an operation part which is installed at the body part and linearly moves by means of the connection driving shaft part; and a needle fixing part which is installed at the operation part.

Here, the drug injecting device fixing part comprises a slider with a protrusion tube to which the body part is engaged, and a plurality of engaging protrusions are formed at an outer surface of the protrusion tube of the slider.

In addition, the body part comprises a body which is formed in a tubular shape and which has an installation hole at its inner side, a partition board with a through hole is formed at the installation hole, and an engaging hole formed at an outer surface of its one side; and a support tube which protrudes in one direction from the partition board of the body and has a guide hole at its inner side.

Here, the body is formed of a curved groove at its skin contact portion.

Furthermore, at an inner surface of the installation hole of the body is formed a support protrusion for a slide grove to be formed.

In addition, the connection driving shaft part is formed of a connection shaft which is engaged to the support tube and the body of the body part, one side of the connection shaft being positioned at the installation hole of the body.

Here, the connection shaft is formed of an engaging member at its one side where the installation hole of the body is formed, and the engaging member has a cut-away groove in a longitudinal direction, and an engaging groove is formed at an outer side where the cut-away groove is formed, and a support shoulder is formed at the center of the connection shaft, and a support surface is formed at the other side where the engaging member is formed.

Furthermore, there is provided an elastic member which is inserted into the connection shaft and of which one side is supported by the support shoulder of the connection shaft, and of which the other side is supported by a partition board of the body.

In addition, the operation part comprises an operation member which is engaged to the installation hole formed at the body of the body part, and a needle installation hole whose one side is open is formed at an inner side of the operation member, and a circumferential groove is formed at an inner surface of the needle installation hole, and to the other side where the needle installation hole is formed is engaged an extension member to which the connection shaft of the connection driving shaft part is engaged.

Here, the extension member has an engaging hole communicating with the needle installation hole of the operation member, and a mounting protrusion formed at its inner surface, onto which mounting protrusion the engaging groove formed at the engaging member of the connection shaft is mounted, and at an outer surface of the extension member is formed a guide protrusion engaged to the slide groove formed at the installation hole of the body.

In addition, the needle fixing part comprises a needle fixing member engaged to the needle installation hole formed at the operation member of the operation part, and a support protrusion is formed at an outer side of the needle fixing member, and at a lower circumferential portion of the support protrusion is formed a circumferential protrusion engaged to the circumferential groove formed at the needle installation hole, and at one side of the needle fixing member are formed a plurality of needle fixing holes, and the needle fixing hole is equipped with a needle which is fixedly engaged for part of the same to expose in an outward direction.

In addition, there is further provided a cover part for covering the needle fixing part.

Here, the cover part is equipped with a cover member covered at the needle fixing member of the needle fixing part, and a height limit member is formed at an inner side of the cover member.

Meanwhile, a jig fixing groove is formed at an inner surface of the needle fixing member of the needle fixing part.

ADVANTAGEOUS EFFECTS

The present invention makes it possible to easily install and disengage a drug injecting device at/from a combined device for skin in such a way the drug injecting device is engaged or disengaged now what an engaging protrusion is formed at a slider of a combined device for skin and an engaging hole to/from which the engaging protrusion formed at the slider is engaged or disengaged in the dermatological drug injecting device.

In addition, the present invention makes it possible to quickly exchange a drug injecting device when it is damaged, in such a way that a drug injecting device can be engaged to or disengaged from a combined device for skin with the aid of a protrusion and a groove.

In addition, the present invention has advantageous features in that a connection shaft advances when a connection lever advances in a state that it is contacting with a connection lever which is configured to transfer the operations of the driving motor of the combined device for skin, and when the connection lever moves backward, the connection shaft elastically recovers by means of an elastic force of an elastic member, with the aid of which construction the connection lever and the connection shaft can be easily disassembled or assembled, and the connection shaft can return back by means of the elastic member, so the connection shaft can work reliably.

In addition, the present invention has advantageous features in that a plurality of needles are equipped, which help form at a time multiple holes at a skin, so it is possible to inject drug into many portions for short time.

In addition, the present invention has advantageous features in that a curved groove is formed at one side of a body part, so the body part can come closer to a skin in an easier way, and it can move along the skin without leaving any scar at the skin.

BEST MODES FOR CARRYING OUT THE INVENTION

The dermatological drug injecting device according to the preferred embodiments of the present invention will be described with reference to the accompanying drawings.

Figure 1:
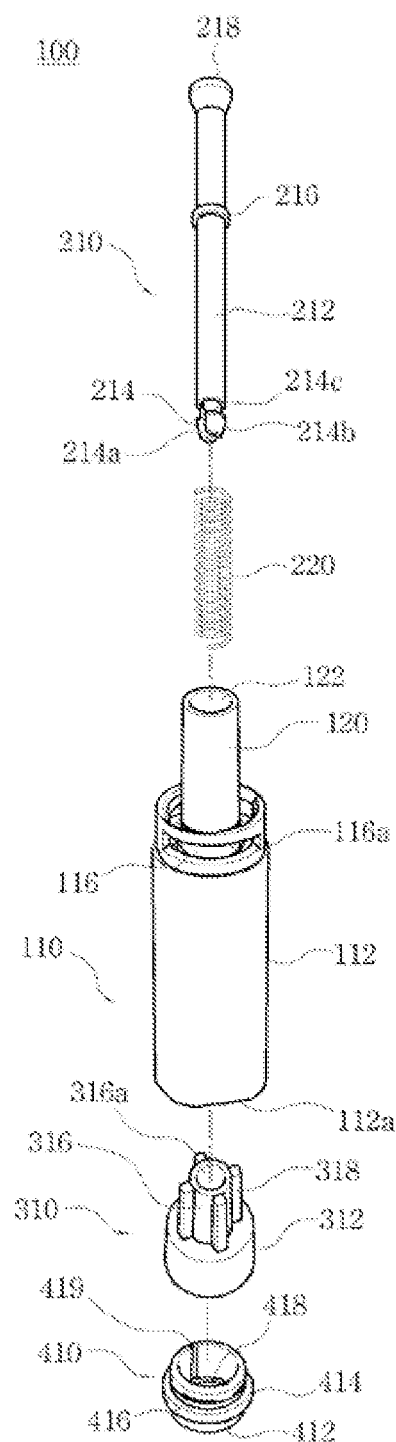
FIG. 1 is a disassembled perspective view illustrating a dermatological drug injecting device according to the present invention.
Figure 2:
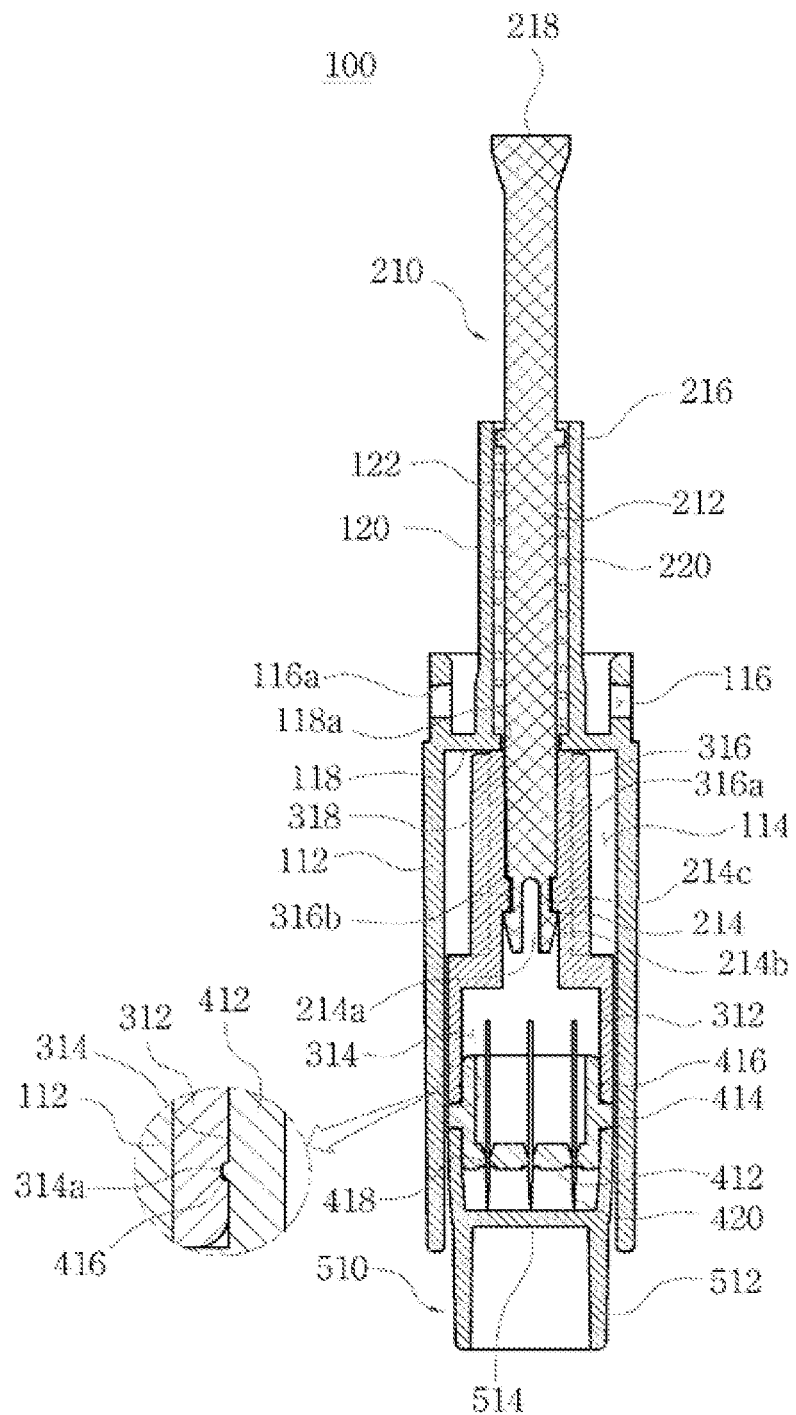
FIG. 2 is a cross sectional view illustrating an engaged state of a dermatological drug injecting device according to the present invention.
Figure 3:
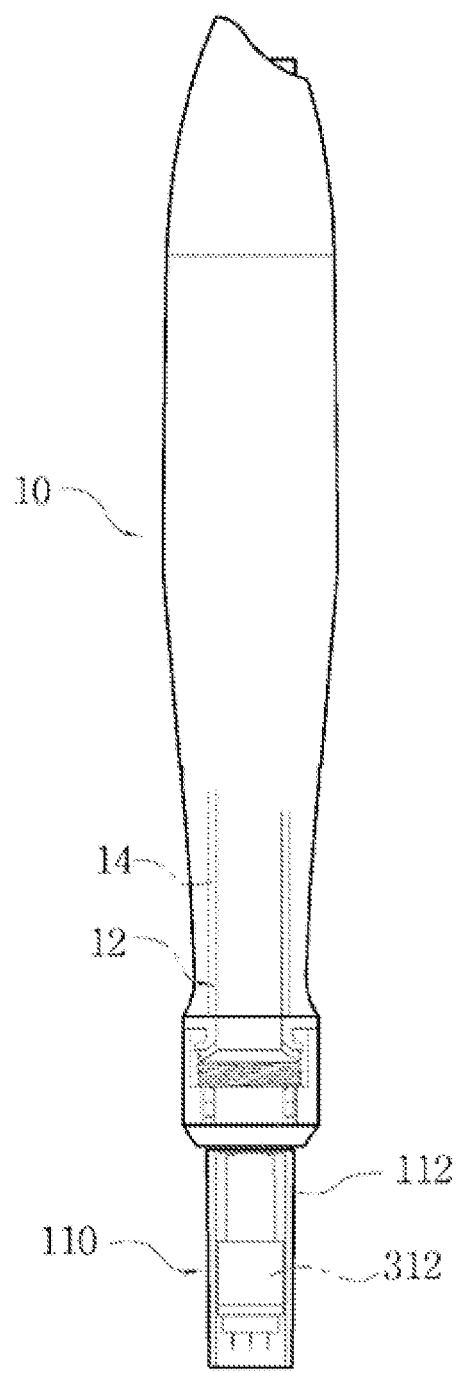
FIG. 3 is a view illustrating a state that a dermatological drug injecting device is engaged to a combined device for skin according to the present invention.
Figure 4:
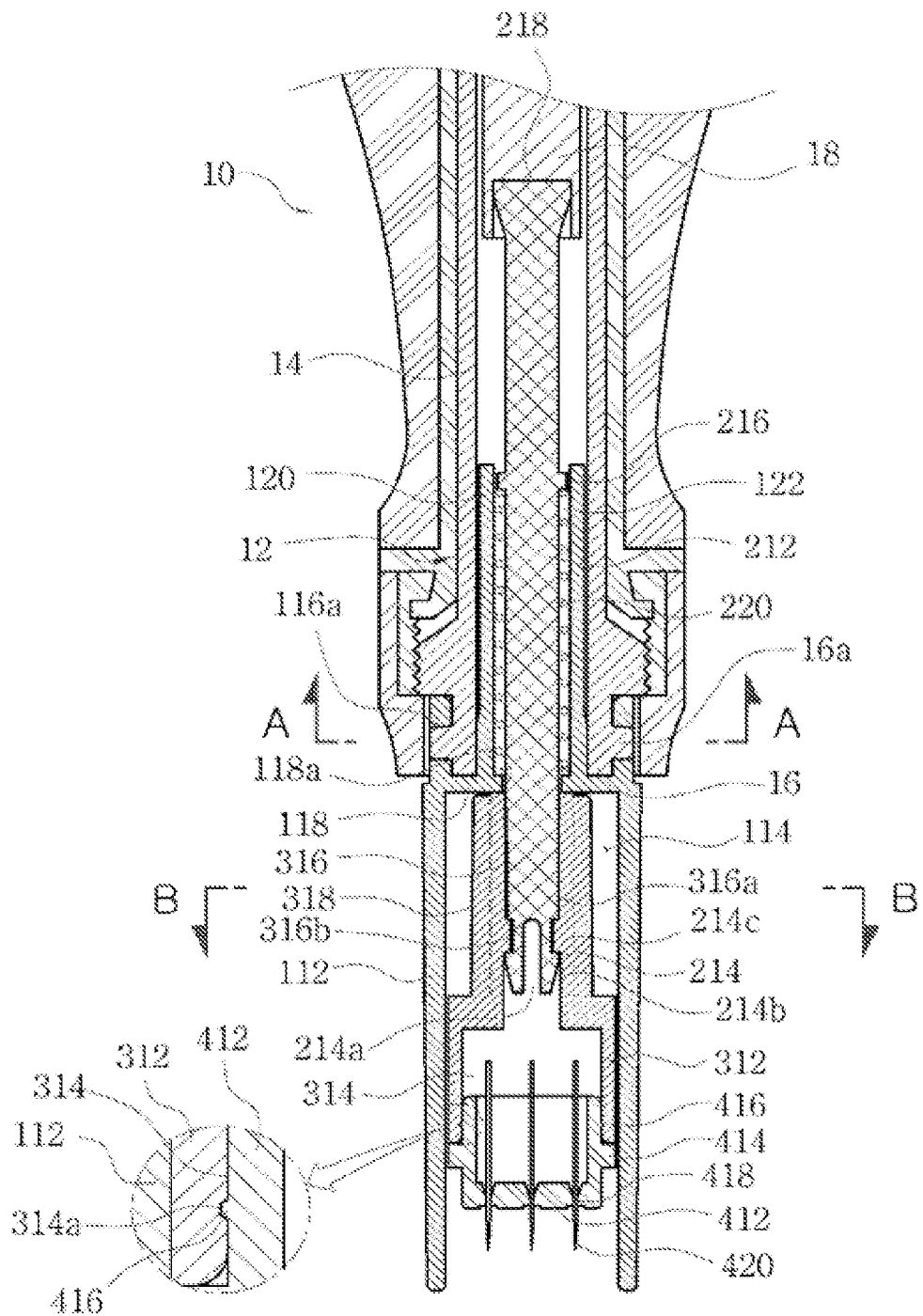
FIG. 4 is a cross sectional view illustrating a state that a dermatological drug injecting device is engaged to a combined device for skin according to the present invention.
Figure 5:
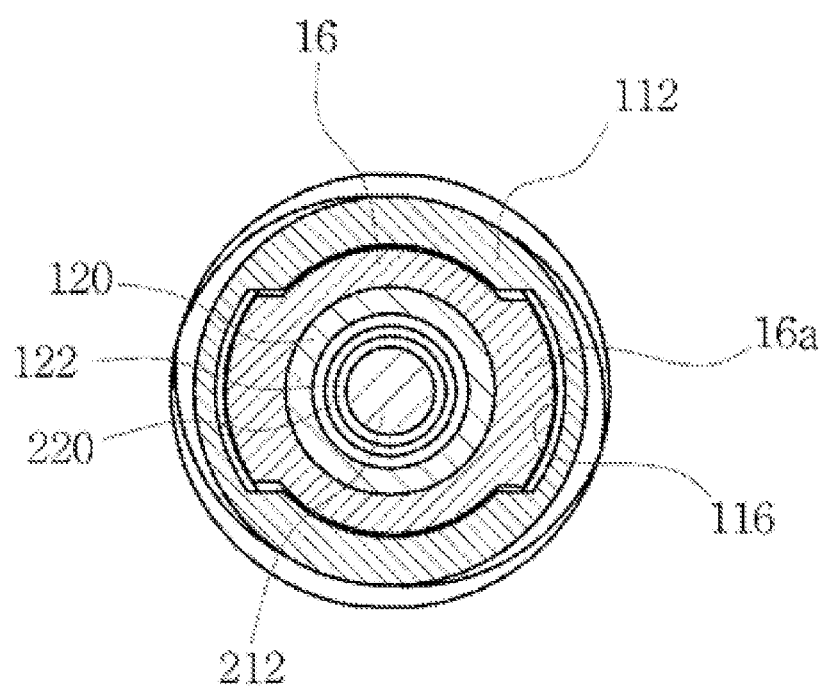
FIG. 5 is a cross sectional view taken along line A-A of FIG. 4.
Figure 6:
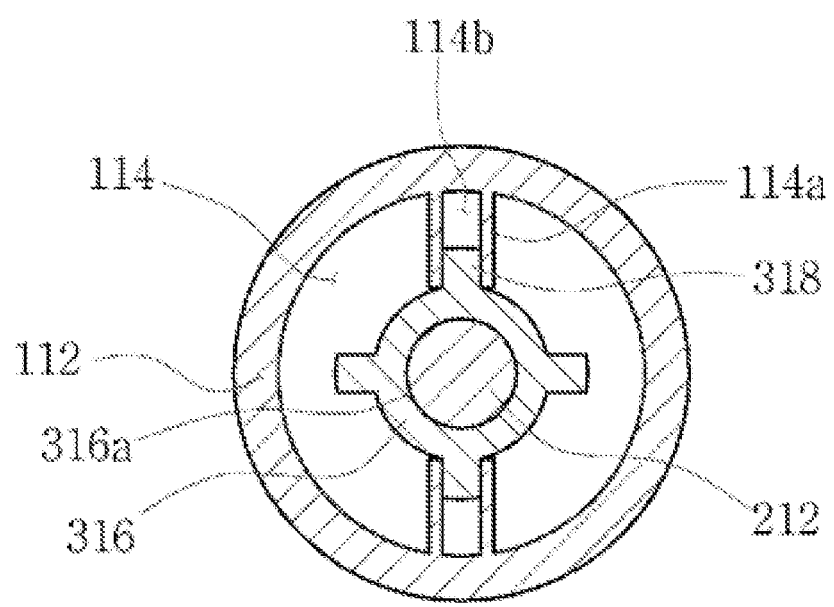
FIG. 6 is a cross sectional view taken along line B-B of FIG. 4.

FIG. 1 is a disassembled perspective view illustrating a dermatological drug injecting device according to the present invention. FIG. 2 is a cross sectional view illustrating an engaged state of a dermatological drug injecting device according to the present invention. FIG. 3 is a view illustrating a state that a dermatological drug injecting device is engaged to a combined device for skin according to the present invention. FIG. 4 is a cross sectional view illustrating a state that a dermatological drug injecting device is engaged to a combined device for skin according to the present invention. FIG. 5 is a cross sectional view taken along line A-A of FIG. 4. FIG. 6 is a cross sectional view taken along line B-B of FIG. 4.

As shown in FIGS. 1 to 6, the dermatological drug injecting device 100 according to the present invention comprises a body part 110 which is fixedly engaged to a drug injecting device fixing part 12 of a combined device 10 for skin.

The body part 110 is formed in a tubular shape and is formed of a body 112 with an installation hole 114 at an inner side.

At an outer surface of one side of the body 112 is formed an engaging hole 116. At the engaging hole 116 is formed an engaging protrusion 116a.

A partition board 118 with a through hole 118a at its center is formed at one side of the installation hole 114 of the body 112, more specifically, at the installation hole 114 in the direction that the engaging hole 116 is formed.

A support tube 120 protrudes from the partition board 118 and is equipped with a guide hole 122 at its inner side.

A curved groove 112a is formed at the other side of the body 112 having the support tube 120, more specifically, at a portion where comes into contact with the skin.

A pair of support protrusions 114a are formed in the longitudinal direction at an inner surface of the installation hole 114 of the body 112, and a slide groove 114b is formed between the pair of the support protrusions 114a.

The combined device 10 for skin to which the body 112 is fixedly engaged is disclosed in the Korean patent registration 10-973628. The body 112 is fixedly engaged to the fixing part 12 of the needle depth adjusting injecting device. The construction on the combined device 10 for skin will not be described in details because it is already disclosed.

In the present invention, the drug injecting device fixing part 12 is equipped with a slider 14, and the slider 14 is equipped with a protrusion tube 16 to which the body 112 is engaged, and an engaging protrusion 16a engaged to the engaging hole 116 of the body 112 is formed at an outer surface of the protrusion tube 16.

The support tube 120 is inserted into the interior of the slider 14. The body 112 is engaged to the protrusion tube 16 of the slider 14. In this state, when the body 112 rotates in one direction, the engaging protrusion 16a comes to engage to the engaging hole 116 formed at the body 112, and at the same time it can be fixed stably by means of the engaging protrusion 116a of the engaging hole 116, so the engaging and disengaging works can be easily performed.

A connection driving shaft part 210 is installed at the body part 110 and performs a linear operation by means of the operations of the combined device 10 for skin which is the prior art.

The connection driving shaft part 210 is equipped with a connection shaft 212 which is engaged to the body 112 and the support tube 120, respectively, one side of which connection shaft 212 being disposed at the installation hole 114 of the body 112, the other side of which being outwardly protruded from the support tube 120.

In addition, at one side of the connection shaft 212 positioned at the installation hole 114 of the body 112 is formed an engaging member 214, and at an outer surface of the connection shaft 212 positioned at the guide hole 122 of the support tube 120 is formed a support shoulder 216, and at the end portion of the other side where the engaging member 214 is formed, is formed a support surface 218 which comes into contact with the connection lever 18 which transfers the operations of the driving motor of the combined device 10 for skin.

The engaging member 214 is equipped with a cut-away groove 214a in the longitudinal direction and a slope surface 214b at its outer surface, and an engaging groove 214c is formed at an end portion of the slope surface 214b.

There is provided an elastic member 220 which is coupled to the connection shaft 212, one side of which elastic member 220 being positioned at the inside of the support tube 120 of the body 112 and being supported by means of the partition board 118 of the body 112.

An operation part 310 is installed at the body 112 of the body part 110 and performs a linear movement by means of the connection driving shaft part 210.

The operation part 310 is equipped with an operation member 312 installed at the installation hole 114 of the body 112, and at the inner side of the operation member 312 is formed a needle installation hole 314 whose one side is open. A circumferential groove 314a is formed in a circumferential direction at the inner surface of the needle installation hole 314.

An extension member 316 with an engaging hole 316a communicating with the needle installation hole 314 protrudes from the other side of the operation member 312, more specifically, from the other side where the needle installation hole 314 of the operation member 312 is formed.

At the engaging hole 316a of the extension member 316 is formed a mounting protrusion 316b onto which the engaging groove 214c of the engaging member 214 is mounted as the engaging member 214 of the connection shaft 212 is engaged. At the outer surface of the extension member 316 is formed a guide protrusion 318 engaged to the slide groove 114b formed at the installation hole 114 of the body 112.

At this time, the connection shaft 212 engaged to the engaging hole 316b of the extension member 316 comes to have an elastic force by means of the cut-away groove 214a of the engaging member 214, so it keeps coming into close contact with the inner surface of the engaging hole 316a.

Therefore, when the connection lever 18 advances, the connection shaft 212 advances in one direction as the connection shaft 212 pressurizes the elastic member, and as the connection shaft 212 advances, the operation member 312 engaged to the engaging member 214 of the connection shaft 212 to advances, so part of the same protrudes from the outer side of the installation hole 114 of the body 112. When the connection lever 18 withdraws, the force applied to the connection shaft 213 disappears, and at the same time, the connection shaft 212 and the operation member 312 returns back by means of an elastic force of the elastic member 220.

A needle fixing part 410 is installed at the operation member 31 of the operation part 310 and performs the same linear movements by means of a linear movement of the operation member 312 for thereby forming holes at the skin.

The needle fixing part 410 is engaged to the needle installation hole 314 of the operation member 312, and at its outer surface is provided a needle fixing member 412 where the support protrusion 414 supported by one side of the operation member 312 is provided.

A circumferential protrusion 416 engaged to the circumferential groove 314a formed at the needle installation hole 314 is formed at an outer surface of the needle fixing member 412, more specifically, an outer surface engaged to the needle installation hole 314 of the operation member 312.

As the circumferential protrusion 416 of the needle fixing member 412 is engaged to the circumferential groove 314a formed at the needle installation hole 314 of the operation member 313, the needle fixing member 412 can be stably engaged to the needle installation hole 314 of the operation member 312.

At one side surface of the needle fixing member 412 are formed a plurality of needle fixing holes 418, and to the needle fixing hole 418 is fixedly engaged a needle 420 whose one side protrudes outwardly.

At this time, the needle 420 is tightly inserted into the needle fixing hole 418 formed at the needle fixing member 412 or can be stably fixed by means of a fixing means such as a bonding, etc. after the needle 420 is fixedly engaged to the needle fixing hole 418.

Therefore, as the needle fixing member 412 repeatedly performs the same operations with the aid of a linear movement of the operation member 312, a plurality of holes can be formed at the skin.

At the inner surface of the needle fixing member 412 is formed a jig fixing groove 419 in the longitudinal direction.

The needle 420 engaged to the needle fixing hole 418 is engaged to the jig (not shown) which adjusts the protrusion length to the outside of the needle fixing member 412 by means of the guide of the jig fixing groove 419 formed at the needle fixing member 412, so the needle 420 is engaged to the needle fixing member 412 by means of the jig, and at the same time, the protrusion length of the needle 420 can be easily adjusted.

The needle 420 fixed at the needle fixing member 412 can be arranged in a circular shape as shown in the drawings, but it is not limited thereto. More specifically, the needles can be arranged in a cubic shape, a rectangular shape, etc.

There is further provided a cover part 510 which is engaged to the needle fixing member 412 and covers the needle 420.

Here, the cover part 510 is equipped with a cover member 512 which is engaged to the needle fixing member 412 with a needle 420 protruding in one direction for thereby covering the needle 420.

When the dermatological drug injecting device 100 is not in use, the needle 420 is covered by the cover member 512 and can be easily moved. When the dermatological drug injecting device 100 is in use, the cover member 512 is removed.

There is further provided a needle height limiting member 514 at the inner side of the cover member 512.

The protrusion length of the needle 420 fixed by the needle fixing member 412 and protruding in one direction can be set to have a certain protrusion length with the aid of the needle height limiting member 514 provided at the inner side of the cover member 512.

The cover member 512 can be selected based on the protruded length of the needle 420 fixed at the needle fixing member 412.

There are provided a plurality of cover members 512 corresponding to the protrusion lengths of the needles 420 fixed at the needle fixing member 412, and the cover member 512 corresponding to a protrusion length of the needle 420 fixed at the needle fixing member 412 is selected among the cover members 512 and is fixed at the needle fixing member 412 so that the protruded needle 420 can be covered.

The operations of the dermatological drug injecting device according to the present invention will be described.

Figure 7:
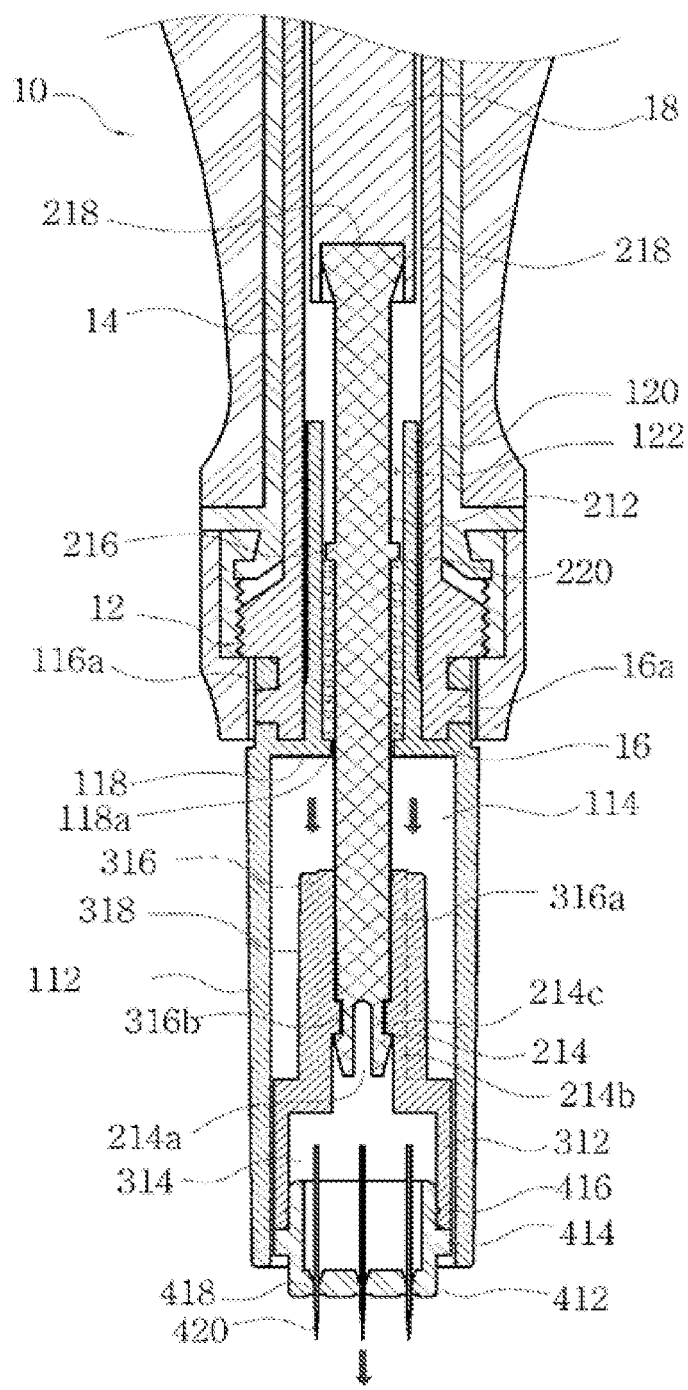
FIG. 7 is a view illustrating an operational relationship on a dermatological drug injecting device according to the present invention and a state that a needle is drawn out.
Figure 8:
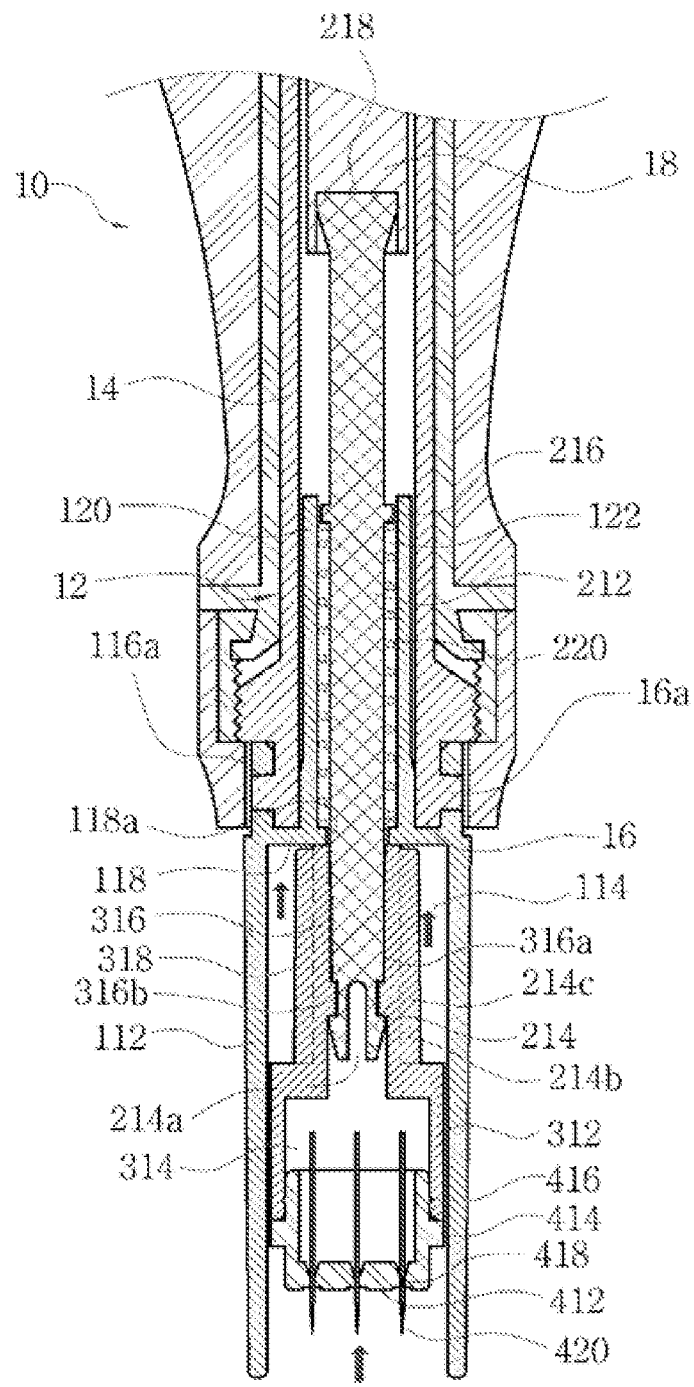
FIG. 8 is a view illustrating an operational relationship on a dermatological drug injecting device according to the present invention and a state that a needle has returned back.

FIG. 7 is a view illustrating an operational relationship on a dermatological drug injecting device according to the present invention and a state that a needle is drawn out. FIG. 8 is a view illustrating an operational relationship on a dermatological drug injecting device according to the present invention and a state that a needle has returned back.

As shown therein, the dermatological drug injecting device 100 of the present invention is directed to fixedly engaging the body 112 to the protrusion tube 16 formed at the drug injecting device fixing part 12 of the combined device 10 for skin.

More specifically, the body 112 is inserted into the protrusion tube 16 of the slider 14, and the body 112 is rotated in one direction, so the engaging protrusion 16a formed at the protrusion tube 16 is engaged to the engaging hole 116 of the body 112 and is supported by the engaging protrusion 116a formed at the engaging hole 116 and is fixed.

At this time, when the body 12 is engaged to the protrusion tube 16 of the slider 14, the support surface 218 of the connection shaft 212 comes into contact with one side of the connection lever 18 of the combined device 10 for skin.

In the above mentioned state, when the combined device 10 for skin is operated, the connection lever 18 performs a linear movement with the aid of the operations of the driving motor (not shown).

At this time, when the connection lever 18 advances, the connection shaft 212 contacting with the connection lever 18 is pushed forward.

When the connection shaft 212 moves forward by the connection lever 18, it moves forward while pressurizing the elastic member 220. As the connection shaft 212 moves forward, the operation member 312 engaged to the connection shaft 212 moves forward by means of the guide of the guide protrusion 318 engaged to the slide groove 114b formed at the installation hole 114 of the body 112.

When the operation member 312 moves forward by means of the connection shaft 212, the needle fixing member 412 engaged to the operation member 312 moves forward and protrudes from the installation hole 114 of the body 112, so holes are formed at the skin by the needle 420.

When the connection lever 18 of the combined device 10 for skin withdraws, the force applied to the connection shaft 212 disappears, and at the same time the connection shaft 212, the operation member 312 and the needle fixing member 412 return back by means of the elastic force of the elastic member 220.

The above mentioned procedures are performed a few times, so the connection shaft 212, the operation member 312 and the needle fixing member 412 perform linear movements for thereby forming numerous holes at the skin.

When the drug or color ink are coated on the surfaces of the skin holes in a state that the holes are formed at the skin by the needles 420, the drug or ink penetrate into the holes formed at the skin.

Since the drug can be directly penetrated into the skin in the above way, so the treatment and skin care effects can be maximized. The holes are formed at the skin in the shapes of characters, symbols or images, and then the color ink is coated on the surfaces of the hole-formed skin, so the ink penetrates into the holes formed at the skin for thereby forming a certain tattoo.

The combined device 10 for skin is disclosed in the Korean patent registration number 10-973628, so the descriptions thereon will be omitted.

The dermatological drug injecting device 100 is installed at the combined device 10 for skin disclosed in the Korean patent registration number 10-973628, and the dermatological drug injecting device 100 can operate by the operations of the combined device 10 for skin.

In the present invention, the dermatological drug injecting device 100 is fixedly installed at the protrusion tube 16 of the slider 14 provided at the drug injecting device fixing part 12 of the dermatological drug injecting device 10 in a one-touch way with the aid of the engaging protrusion 16a and the engaging hole 116 of the body 12, so the dermatological drug injecting device 100 can be easily engaged to or disengaged from the combined device 10 for skin, whereby the maintenance and the exchange work of the dermatological drug injecting work 100 can be easily performed.

The curved groove 112a is formed at one side of the body 112, more specifically, at the surface directly contacting with the skin, so it can be moved with the body 112 contacting with the skin without causing any damages at the skin in the middle of the movement.

Since the drug is injected into the curved groove 112a formed at one side of the body while scratching the drug coated on the skin after numerous holes are formed at the skin using the needles 420, the drug can be injected without leaving any damages to the skin.

The connection shaft 212 and the connection lever 18 of the combined device 10 for skin are not engaged by means of the engaging means, and the support surface 218 of the connection shaft 212 comes into contact with the connection lever 18, so the connection shaft 212 operates by means of the operations of the connection lever 18, whereby it is possible to easily engage or disengage the dermatological drug injecting device 100.

The connection shaft 212 and the connection lever 18 of the combined device 10 for skin are not engaged by means of the engaging means, and the connection shaft 212 comes into contact with the connection lever 18, so the connection shaft 212 can operate by the operations of the connection lever 18, whereby the dermatological drug injecting device of the present invention is forced to move back, but returns back by the elastic force of the elastic member 220, which makes it possible to prevent the connection shaft 212 from being damaged by the friction force with the inner surfaces of the connection shaft 212 and the body 112 and the support tube 120.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

INDUSTRIAL APPLICABILITY

The present invention is directed to a dermatological drug injecting device which is industrially advantageous now that the present invention makes it possible to treat wrinkles, keratin, scar, melasma, dried and split skins, hair loss, etc. in a human body and makes it possible to inscribe images or characters using a pigment.

The invention claimed is:

1. A dermatological drug injection device which is engaged to a combined device for skin, comprising:
    a body part which is engaged to a dermatological drug injecting device fixing part of the combined device for skin;
    a connection driving shaft part which is installed at the body part and linearly moves;
    an operation part which is installed at the body part and linearly moves by means of the connection driving shaft part; and
    a needle fixing part which is installed at the operation part,
    wherein the body part includes a body which is formed in a tubular shape and which has an installation hole at its inner side, a partition board with a through hole is formed at the installation hole, and an engaging hole formed at an outer surface of its one side; and a support tube which protrudes in one direction from the partition board of the body and has a guide hole at its inner side, and
    wherein at an inner surface of the installation hole of the body is formed a support protrusion for a slide grove to be formed.

2. The device of claim 1, wherein the drug injecting device fixing part comprises a slider with a protrusion tube to which the body part is engaged, and a plurality of engaging protrusions are formed at an outer surface of the protrusion tube of the slider.

3. The device of claim 1, wherein the body is formed of a curved groove at its skin contact portion.

4. The device of claim 1, wherein the connection driving shaft part is formed of a connection shaft which is engaged to the support tube and the body of the body part, one side of the connection shaft being positioned at the installation hole of the body.

5. The device of claim 4, wherein the connection shaft is formed of an engaging member at its one side where the installation hole of the body is formed, and the engaging member has a cut-away groove in a longitudinal direction, and an engaging groove is formed at an outer side where the cut-away groove is formed, and a support shoulder is formed at the center of the connection shaft, and a support surface is formed at the other side where the engaging member is formed.

6. The device of claim 4, wherein there is provided an elastic member which is inserted into the connection shaft and of which one side is supported by the support shoulder of the connection shaft, and of which the other side is supported by a partition board of the body.

7. The device of claim 1, wherein the operation part comprises an operation member which is engaged to the installation hole formed at the body of the body part, and a needle installation hole whose one side is open is formed at an inner side of the operation member, and a circumferential groove is formed at an inner surface of the needle installation hole, and to the other side where the needle installation hole is formed is engaged an extension member to which the connection shaft of the connection driving shaft part is engaged.

8. The device of claim 7, wherein the extension member has an engaging hole communicating with the needle installation hole of the operation member, and a mounting protrusion formed at its inner surface, onto which mounting protrusion the engaging groove formed at the engaging member of the connection shaft is mounted, and at an outer surface of the extension member is formed a guide protrusion engaged to the slide groove formed at the installation hole of the body.

9. The device of claim 1, wherein the needle fixing part comprises a needle fixing member engaged to the needle installation hole formed at the operation member of the operation part, and a support protrusion is formed at an outer side of the needle fixing member, and at a lower circumferential portion of the support protrusion is formed a circumferential protrusion engaged to the circumferential groove formed at the needle installation hole, and at one side of the needle fixing member are formed a plurality of needle fixing holes, and the needle fixing hole is equipped with a needle which is fixedly engaged for part of the same to expose in an outward direction.

10. The device of claim 1, further comprising a cover part for covering the needle fixing part.

11. The device of claim 10, wherein the cover part is equipped with a cover member covered at the needle fixing member of the needle fixing part, and a height limit member is formed at an inner side of the cover member.

12. The device of claim 1, wherein a jig fixing groove is formed at an inner surface of the needle fixing member of the needle fixing part.

\* \* \* \* \*